(12) United States Patent
Policello et al.

(10) Patent No.: US 6,534,077 B2
(45) Date of Patent: Mar. 18, 2003

(54) ORGANOSILOXANE CONTAINING MODIFIED GROUPS IN AGRICULTURAL COMPOSITIONS

(75) Inventors: George A. Policello, Ossining, NY (US); Gerald J. Murphy, Hopewell Junction, NY (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 09/861,151

(22) Filed: May 18, 2001

(65) Prior Publication Data
US 2002/0002114 A1 Jan. 3, 2002

Related U.S. Application Data

(60) Provisional application No. 60/205,962, filed on May 19, 2000.
(51) Int. Cl.$^7$ ................................. A10N 25/02
(52) U.S. Cl. ........................ 424/405; 556/444; 556/445; 568/673; 528/31; 528/28; 528/27; 528/25; 525/474; 525/477; 524/287; 524/588; 524/189; 524/190; 524/211; 504/116.1

(58) Field of Search .................................. 556/444, 445; 568/673; 528/31, 28, 27, 25; 525/477, 474; 524/588, 189, 190, 211, 287; 504/116.1; 424/405

(56) References Cited

U.S. PATENT DOCUMENTS 5,683,685 A  * 11/1997 Hirano et al.
5,998,331 A  * 12/1999 Policello \* cited by examiner Primary Examiner—Robert Dawson
Assistant Examiner—Kuo-Liang Peng
(74) Attorney, Agent, or Firm—Michael P. Dilworth

(57) ABSTRACT

The present invention teaches modified organosilicone and their use, a preferred of which is as adjuvants for pesticides. The modified organosilicone have siloxane backbones with pendant, terminal or intermediate amine and polyether groups. The modified groups or the siloxane may be functionalized further with alkyl or alkyleneoxide groups.

33 Claims, No Drawings

ORGANOSILOXANE CONTAINING MODIFIED GROUPS IN AGRICULTURAL COMPOSITIONS

CROSS REFERENCE TO RELATED APPLICATION

This application claims priority from U.S. Provisional Application No. 60/205,962, filed on May 19, 2000.

BACKGROUND OF THE INVENTION

Many herbicides require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are provided either as a tankside additive or used as a component in herbicide formulations.

Gaskin, et al., Pestic. Sci. 1993, 38, 185–192, demonstrated that some trisiloxane ethoxylates (TSE), such as Silwet L-77® surfactant (available from Witco Corp. of Greenwich, Conn.), can antagonize cuticular penetration of a herbicide into grasses, when compared to the herbicide alone. The term antagonism is used to indicate that the treatment of herbicide plus adjuvant is less effective than the comparative herbicide treatment.

Sandbrink, et al., (Pest. Sci. 1993, 38, 272–273, published that a TSE antagonized glyphosate performance relative to glyphosate alone in the control of *Panicum maximum* Jacq. Snow, et al., Langmuir, 1993, 9, 424–30, discusses the physical properties and synthesis of novel cationic siloxane surfactants. These siloxanes are based on the reaction of chloro propyl modified trisiloxane with an alkanolamine, such as N-methylethanolamine, which was further reacted with a halide to make a quaternary surfactant.

Petroff, et al., EP 92116658, describes the use of cationic, quaternary trisiloxanes to enhance the efficacy of glyphosate on velvetleaf, a broadleaf weed. Henning, et al., (DE 4318537) describes cationic siloxanyl modified polyhydroxy hydrocarbon or carbohydrate for use with plant protection agents. These compounds are derived from a saccharide containing 1 to 10 pentose and/or hexose units, modified with a quaternary ammonium group, and a siloxane moiety.

Reid, et al., U.S. Pat. No. 3,389,160 describes amino modified siloxane alkoxylates where the amino functionality appears as the terminal group on the alkyleneoxide moiety, opposite the siloxane group.

Policello in U.S. Pat. No. 5,998,331 discloses amino modified siloxanes wherein the amine is bound by an ether bond to the siloxane backbone wherein the amine may be terminal or pendant to the backbone.

SUMMARY OF THE INVENTION

It has now been discovered that an organosiloxane copolymer containing separate terminal or pendant amino-containing and polyether-containing functional groups are useful as adjuvants and additives for applications with herbicides.

Optionally, the modified organosiloxanes of this invention may be blended with conventional trisiloxane alkoxylates (TSAs). Blends of these modified organosiloxanes with TSAs provide enhanced wetting properties on difficult to wet plant surfaces.

Additionally the modified organosiloxanes of this invention may be blended with conventional organic surfactants, as emulsifiers, dispersants, coadjuvants or cosurfactants.

DETAILED DESCRIPTION OF THE INVENTION

The modified organosiloxanes are useful as adjuvants for herbicide applications.

Modified Organosiloxanes:

The modified organosiloxanes of the present invention preferably are amino polyether siloxanes and have the average general formula:

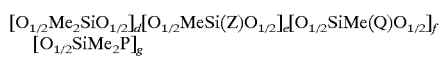

where d is 0 to 2; e is >0 and <4, preferably >0 to 2; f≧0 and <4, most preferably >0 to 2; g is 2 if the siloxane is not cyclic or zero if the siloxane is cyclic; d+e+f+g≦6; $Z=C_nH_{2n}O(C_aH_{2a}O)_wR^1$; n=2 to 4, preferably 3; a=2–4, preferably 2; w=1 to 30; $R^1$ is hydrogen, or a hydrocarbon radical between 1 and 4 carbon atoms; $Q=B(O)_jR^2N(R^3)_2$; B is a divalent bridging group of $C_1$ to $C_6$, preferably $C_3$ to $C_4$; $R^2$ is a divalent organic group containing 2 to 8 carbons, preferably 3 to 4 carbons, each optionally OH substituted; j is 0 or 1, preferably 1; $R^3$ is hydrogen, an amino alkyl of one to four carbons, an alkyl of 2 to 4 carbon atoms, an alkyl of 2 to 4 carbon atoms substituted with one or more hydroxy groups or a polyether of the general structure —$(C_aH_{2a}O)_bR^4$; each a is 2 to 4, preferably 2 to 3; each b is 2 to 30, preferably 2 to 8; the $R^4$ groups independently are hydrogen or a group of 1 to 4 carbons; and P is Q or, provided f is not 0, methyl.

Preferably a is such that there is a mixture of ethylene oxide (EO), propylene oxide (PO) units and butylene oxide (BuO) units, where a=2 and 4. Preferably, for aqueous applications, there is a preponderance of EO units, most preferably every a=2. For non-aqueous applications, such as crop oil concentrates, there may be more PO and BuO units. When Z or $R^3$ contain a mixture of oxyalkylenes, the different oxyalkylene groups may be arranged in blocked or random manner. One skilled in the art will understand the advantages in the position of the oxyethylene relative to the oxypropylene, when the alkyleneoxide group is blocked.

The Q groups may include protonated amines, i.e., where there is a hydrogen atom attached to the nitrogen in the Q group, which can occur to the aminosilicon alkoxylates under acidic conditions. Also contemplated herein are quaternary versions of Q, i.e., where there is a third $R^3$ group on the nitrogen in Q. Quaternarization may be accomplished in conventional manner. In either such case, i.e., protonated or quaternarized Q, the group Q may be represented by the formula:

OTHER SOLIXANES

In addition, the compositions of the present invention optionally may include TSAs of the general formula:

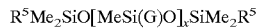

Wherein x=0 to 2, preferably 1; $G=C_nH_{2n}O(C_2H_4O)_t(C_3H_6O)_wR^6$; n=2 to 4, preferably 3; t=3 to 20, preferably 4 to 8; w=0 to 8, providing that when w is >0, (t+w) is preferably between 5 and 12; $R^6$ is hydrogen, acetyl or a hydrocarbon radical between 1 and 4 carbon atoms; and $R^5$ is G, or an alkyl of one to four carbons. The preferred nonionic siloxane alkyoxylates are trisiloxane alkoxylates, where x=1, n=3, t=4 to 8, w=0, $R^5$ is Me, $R^6$ is H or Me.

PESTICIDES

The compositions of the present invention also optionally include pesticides, especially acid functionalized ones, i.e., compounds that contain at least one carboxylic, sulfonic or phosphonic acid group or their salt or ester. The term pesticide means any compound used to destroy pests, e.g., rodenticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

EXCIPIENTS

The compositions also may include fatty acid esthers, e.g., methyl soyate, for crop oil concentrate formulations, as well as water, for aqueous applications. Buffers, preservatives and other standard excipients known in the art also may be included in the composition. When the compositions of the present invention are insoluble in distilled water, spreading may be achieved by the addition of a small amount of an acid, such as acetic acid, to protonate the amine functionality, thereby increasing water solubility. Moreover, other cosurfactants which do not interfere with superspreading, may be included, for instance cosurfactants which have short chain hydrophobes ($C_{10}$ or less, not counting any branching carbons) or alkyleneoxide copolymers such as sold under the trademarks PLURONIC® and TETRONIC® (both BASF Corp.) and UCON® (Union Carbide/Dow Corp). Examples of such cosurfactants and their use can be found in U.S. Pat. No. 5,104,647, U.S. Pat. No. 5,558,806 and EP 0862857, all incorporated herein by reference.

MANUFACTURE

The modified organosiloxanes of the present invention may be made by the hydrosilation of a hydridosiloxane with an epoxy intermediate, such as allyl glycidyl ether, vinyl cyclohexene monoxide, along with an allyl polyalkyleneoxide, which may be reacted sequentially, or as a premix of the epoxy and allyl polyalkyleneoxide intermediates. This is followed by ring opening the epoxide with the appropriate amino group. The hydridosoxanes described are commercially available and may be made as known in the art. Hydrosilation conditions are within the general conditions taught in Marciniec (*Comprehensive Handbook of Hydrosilylation*, Edited by Bogdan Marciniec, Pergamon Press).

Instead of an epoxy ring opening, it is also possible to prepare an amino polyether silicone useful in the invention by hydrosilating both an unsaturated amine such as methallyl amine, N-allyl-N, N-dimethylamine, N-allyl-N, N-diethylamine, N-allyl-N-methylamine and an unsaturated polyether, simultaneously or sequentially, to give a product as described above, where j is 0.

The nonionic siloxane and the pesticides are commercially available and their manufacture is known in the art.

USE

The modified organosiloxanes may be used in agricultural applications as adjuvants for pesticides, wherein the siloxane is applied in a pesticide formulation to agricultural products. The composition of the present invention is useful as a tankside additive, or as a component in a herbicide formulation. In addition the compositions of the present invention are useful as adjuvants for other pesticides, such as, fungicides, insecticides, plant growth regulators, acaracides and the like. The pesticide formulations may be wet, dry, slurries or other formulations as are known in the art.

The siloxanes are added directly to a spray tank along with an acid functional pesticide, or as part of a pesticide formulation. When used as a tankside additive, the siloxane is present at weight concentrations between 0.001% and 5.0%, preferably between 0.025% and 0.5%. Likewise, when the modified organosiloxanes are used in a pesticide formulation (In-can), they are present at weight concentrations that will deliver between 0.001% and 5.0% to the final use dilution, preferably between 0.025% and 0.5%, of the final use dilution.

It is noted that most dilutions will be made with water, but in the case of crop oil concentrates, oils (mineral, silicone, animal or vegetable oils) will be the diluents.

When the compositions of the present invention are used in conjunction with a TSA, the weight ratio of the TSA to the modified organosiloxanes is between 5:95 and 95:5, preferably between 5:95 and 40:60. The blend may be accomplished by mixing physically the two components prior to use, or by adding them separately to a spray mixture at the point of use.

When the compositions of the present invention are used in conjunction with nonsilicone surfactants, the weight ratio of the nonsilicone surfactant to the modified organosiloxane is between 1:99 and 99:1, preferably between 99:1 and 40:60.

The modified organosiloxanes also may be used generally as surface active agents in aqueous formulation where there is an acid functionalized component. The modified organosiloxanes also may be used as surface active agents, including, but not limited to, as surfactants, wetting agents and softeners for textiles, flow and leveling agents in coatings, hair care products, skin care and creams for personal care applications and anti-static agents, detergents and softeners for laundry products.

The invention is illustrated by the following non-limiting examples.

EXAMPLES

Unless otherwise indicated, all parts and percentages are by weight, and are based on the weight at the particular stage of the processing being described.

Example 1 a. Invention Siloxanes

Amino polyether siloxanes of the present invention may be prepared by the hydrosilation of a low molecular weight SiH intermediate with allyl glycidyl ether and an allyl polyalkyleneoxide. The resulting epoxy polyether siloxane is then ring-opened with the desired amine to yield the amino polyether siloxane. The epoxy polyether siloxane synthesis is known in the art as described under manufacture.

Therefore 50 g (0.0834 moles) of such an epoxy, polyether siloxane (6.7 wt % $C_2O$), 11.4 g (0.1084 moles) diethanolamine and 26.3 g isopropanol were weighed into a 250 mL 4 neck round bottom flask, equipped with a heating mantle, mechanical stirrer, thermometer and reflux condenser containing a nitrogen by-pass. The mixture was heated to 80° C. and catalyzed with 0.09 g of titanium IV butoxide and maintained at this temperature for a total 9 hours. The mixture was cooled to 55° C. and 0.4 mL of distilled water was added to deactivate the catalyst, while stirring for 1 hour. The mixture was then filtered and stripped on a rotary evaporator for 1.5 hours at ~1 mm Hg pressure to yield an amber colored liquid with a viscosity of 670 cps (Brookfield LV-3, 100 rpm). The product is listed in Table 1 as SIL-3. Other compositions of amino, polyether siloxanes may be prepared according to this procedure. Table 1 provides a description of additional amino, polyether siloxanes used herein as illustrative examples.

TABLE 1

Description of Modified Organosiloxanes

| Invention | X | Y | Description |
|---|---|---|---|
| SIL-1 | 1.3 | 0.6 | Q = $C_3H_6OCH_2CH(OH)CH_2$—$N[C_2H_4OH]_2$ |
| | | | Z = $C_3H_6O$ $(C_2H_4O)_8$ $CH_3$ |
| SIL-2 | 0.95 | 0.95 | Q = $C_3H_6OCH_2CH(OH)CH_2$—$N[C_2H_4OH]_2$ |
| | | | Z = $C_3H_6O$ $(C_2H_4O)_8$ $CH_3$ |
| SIL-3 | 0.6 | 1.3 | Q = $C_3H_6OCH_2CH(OH)CH_2$—$N[C_2H_4OH]_2$ |
| | | | Z = $C_3H_6O$ $(C_2H_4O)_8$ $CH_3$ | b. Comparative Silicone Based Surfactants:

Table 2 describes the comparative silicone based surfactants. These materials were prepared by standard hydrosilation of the corresponding hydridosiloxane and allyl polyalkyleneoxide, and are of the general structure:

$Me_3SiO[Me_2SiO]_x[MeSi(Z)O]_ySiMe_3$

It is important to note here that SIL-B is prepared from the same hydridosiloxane intermediate as the examples of the present invention listed in Table 1. The key difference is that SIL-B is only modified with allyl polyalkyleneoxide (Same 8 EO intermediate used in SIL-1–3), but does not contain the amine functionality found in the modified organosiloxane compositions of the present invention.

TABLE 2

Comparative Silicone Based Surfactants

| Reference | X | Y | Description |
|---|---|---|---|
| SIL-A | 0 | 1 | Z = $C_3H_6O$ $(C_2H_4O)_8H$ |
| SIL-B | 0 | 1.9 | Z = $C_3H_6O$ $(C_2H_4O)_8CH_3$ | c. Comparative Nonsilocone Surfactants:

Table 3 provides descriptions of typical, comparative, nonsilicone surfactants.

TABLE 3

Description of Comparative Conventional Nonsilicone Surfactants

| Reference | Moles EO | Remarks |
|---|---|---|
| OPE | 10 | Octylphenol ethoxylate (TRITON ® X-100) (Union Carbide Corp., Danbury, CT) |
| TAE | 12 | Tallow amine ethoxylate (Witcamine 412) (CK Witco Corporation, Greenwich, CT) |

Example 2

This example demonstrates the utility of the modified organosilicone composition of the present invention as surfactants and spreading agents. Surface tension was measured using a Cahn microbalance, with a sand blasted platinum blade as the sensor. Solutions of the various components were prepared at 0.1 wt % in 0.005M NaCl water (deionized), as an equilibrium aid.

Aqueous solutions of these unique compositions provide a significant reduction in surface tension relative to conventional surfactants. Also the amine moiety, contained in the compositions of this present invention, does not detract from the surface tension lowering associated with traditional trisiloxane alkoxylates (Sil-A), as shown in Table 4.

Spreading was determined by applying a 10 mL droplet of surfactant solution onto an acetate film (Crystal Clear Write on Film, USI Inc., Brandford, Conn.) and measuring the spread diameter after 30 seconds. The solution was applied with an automatic pipette to provide droplets of reproducible volume. Deionized water that was further purified with a Millipore filtration system was used to prepare the surfactant solutions.

The compositions of the present invention, and SIL-A and SIL-B, provide enhanced spreading relative to conventional surfactants, OPE and TAE. However, the added amine functionality, contained in the compositions of this present invention, unexpectedly gives an improvement in the spreading properties, when compared to SIL-B, which is the corresponding non-amine containing siloxane surfactant (Table 4).

TABLE 4

Comparison of Aqueous Surface Tension Properties

| | Surface Tension | Spread Diameter (mm) | |
|---|---|---|---|
| Surfactant | (mN/m, 0.1 wt %) | 0.1 wt % | 0.2 wt % |
| SIL-1 | 22 | 27 | 46 |
| SIL-2 | 22 | 31 | 46 |
| SIL-3 | 21 | 32 | 48 |
| SIL-4 | 21 | 51 | 59 |
| SIL-5 | 23 | 16 | 25 |
| OPE | 29 | nd | 10 |
| TAB | 38 | nd | 8 |
| None[b] | 72 | * | — |

[a]Surface tension in mN/m at 25° C.
[b]Surface tension of water from CRC Handbook of Chenistry and Physics; 63 Edition, 1982–1983.
*Spread diameter of distilled water = 4 mm a. Surface tension in mN/m at 25° C.
b. Surface tension of water from *CRC Handbook of Chemistry and Physics;* 63 Edition, 1982–1983.
* Spread diameter of distilled water=4 mm Example 3

This example demonstrates the ability of the compositions of the present invention to overcome the antagonism associated, with trisiloxane ethoxylates (i.e. SIL-A), on the efficacy of glyphosate, for control of grasses.

Barnyardgrass (*Echinochloa crus-galli*) 10 cm in height were treated with 0.75 wt % (a.i.) glyphosate, isopropylamine salt (Monsanto), either alone, or plus a spray adjuvant (0.05 and 0.1 wt % respectively). The spray was applied at 100 L/ha using a T-Jet 8002E nozzle. The plants were subjected to simulated rainfall (2.5 cm), 2 h after herbicide application, to determine the rainfastening ability of the adjuvants. Plants were evaluated at week 1 and 2 weeks after treatment, by visual observation, relative to the untreated check. A score of 0 means no plant injury, while a score of 100 indicates total control (burndown, with no regrowth).

The effect of adjuvant, on barnyardgrass control by glyphosate isopropylamine salt (IPA), is shown in Table 5. Herbicide effects become more obvious at 1 week after treatment (WAT) with the compositions of the present invention, while the standard TSA (SIL-A) is no more effective than herbicide alone (Treatment 9). At 2 WAT the herbicide applications with SIL-1, SIL-2 and SIL-3 were significantly more effective than those with SIL-A or herbicide alone.

TABLE 5

Effect of Adjuvant on Glyphosate-IPA Efficacy on Barnyardgrass

| Treatment | Adjuvant | Wt % Adjuvant | Percent Control [1] 1 WAT | 2 WAT |
|---|---|---|---|---|
| 1 | SIL-1 | 0.1 | 80.0a | 83.75a |
| 2 | SIL-1 | 0.05 | 71.3a | 72.5a |
| 3 | SIL-2 | 0.1 | 76.3a | 80.0a |
| 4 | SIL-2 | 0.05 | 58.5b | 81.25a |
| 5 | SIL-3 | 0.1 | 38.8c | 73.75a |
| 6 | SIL-3 | 0.05 | 12.5d | 40.0b |
| 7 | SIL-A | 0.1 | 6.8d | 12.5c |
| 8 | SIL-A | 0.05 | 15.0d | 21.25c |
| 9 | None [2] | None | 7.5d | 18.75c |
| 10 | Untreated | — | 0e | 0d |

[1] Within columns, values with the same letter are not significantly different according to Duncan's Multiple Range Test; p = 0.05.
[2] Treatment 9 = glyphosate-IPA without adjuvant.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

What is claimed is:

1. A composition comprising a) a siloxane having separate polyether and amino functional groups thereon and b) a pesticide.

2. A composition as in claim 1 wherein component a) is an amino polyether siloxane of the following formula:

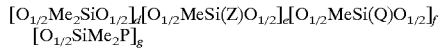

where d is 0 to 2; e is >0 and <4; f≧0 and <4; g is 2 if the siloxane is not cyclic or zero if the siloxane is cyclic; d+e+f+g≦6; $Z=C_nH_{2n}O(C_aH_{2a}O)_wR_1$; n=2 to 4; a=2–4; w=1 to 30; $R^1$ is hydrogen, or a hydrocarbon radical between 1 and 4 carbon atoms; $Q=B(O)_jR^2N(R^3)_2$ or $B(O)_jR^2N^+(R^3)_3$; B is a divalent bridging group of $C_1$ to $C_6$, $R^2$ is a divalent organic group containing 2 to 8 carbons, each optionally OH substituted; j is 0 or 1; $R^3$ is hydrogen, an amino alkyl of one to four carbons, an alkyl of 2 to 4 carbon atoms, an alkyl of 2 to 4 carbon atoms substituted with one or more hydroxy groups or a polyether of the general structure—$(C_aH_{2a}O)_bR^4$; each a is 2 to 4; each b is 2 to 30; the $R^1$ groups independently are hydrogen or a hydrocarbon group of 1 to 4 carbons; and P is Q or, provided f is not 0, methyl.

3. A composition as in claim 1 wherein the pesticide is an acid functional pesticide.

4. A composition as in claim 1 further comprising a trisiloxane alkoxylate of the formula;

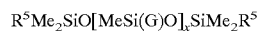

Wherein x=0 to 2; $G=C_nH_{2n}O(C_2H_4O)_t(C_3H_6O)_wR^6$; n=2 to 4; t=3 to 20; w=0 to 8; $R^6$ is hydrogen, acetyl or a hydrocarbon radical between 1 and 4 carbon atoms; and $R^5$ is G, or an alkyl of one to four carbons.

5. A composition as in claim 4 wherein the weight basis ratio of the trisiloxane alkoxylate to the component a) is between 5:95 and 95:5.

6. A composition as in claim 1 additionally comprising a nonionic surfactant.

7. A composition as in claim 2 wherein in the group Z there is a mixture of ethylene oxide with propylene oxide and/or butylenes oxide groups.

8. A composition as in claim 1 further comprising a water or oil diluent.

9. A composition as in claim 8 where the siloxane a) is present at a concentration of from 0.001% to 5.0% by weight.

10. A composition as in claim 1 where the pesticide is selected from the group consisting of: growth regulators, photosynthesis inhibitors, pigment inhibitors, mitotic disrupters, lipid biosynthesis inhibitors, cell wall inhibitors, and cell membrane disrupters.

11. A composition as in claim 1 wherein the pesticide is a herbicide selected from the group consisting of: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalim, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

12. A composition formed by mixing at least two components:

a) an amino polyether siloxane of the following formula:

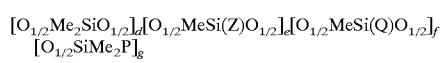

where d is 0 to 2; e is>0 and <4; f>0 and <4; g is 2 if the siloxane is not cyclic or zero if the siloxane is cyclic; d+e+f+g<6; $Z=C_nH_{2n}O(C_aH_{2a}O)_wR^1$; n=2 to 4; a=2–4; w=1 to 30; $R^1$ is hydrogen, or a hydrocarbon radical between 1 and 4 carbon atoms; $Q=B(O)_jR^2N(R^3)_2$ or $B(O)_jR^2N+(R^3)_3$;

B is a divalent bridging group of $C_1$ to $C_6$; $R^2$ is a divalent organic group containing 2 to 8 carbons, each optionally OH substituted; j is 0 or 1; $R^3$ is hydrogen, an amino alkyl of one to four carbons, an alkyl of 2 to 4 carbon atoms, an alkyl of 2 to 4 carbon atoms substituted with one or more hydroxy groups or a polyether of the general structure—$(C_aH_{2a}O)_bR^4$; each a is 2 to 4; each b is 2 to 30; the $R^4$ groups independently are hydrogen or a hydrocarbon group of 1 to 4 carbons; and P is Q or, provided f is not 0, methyl; and b) an acid functional component.

13. A composition of claim 12 further comprising water.

14. A process for wetting a surface of a substrate comprising applying a composition as in claim 13 to a surface of a substrate.

15. A process for treating plants comprising applying to plants a superspreading composition comprising (a) an amino polyether siloxane of the formula:

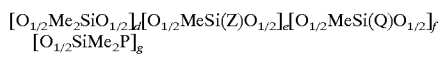

where d is 0 to 2; e is >0 and <4; f≧0 and <4; g is 2 if the siloxane is not cyclic or zero if the siloxane is cyclic; d+e+f+g≦6; $Z=C_nH_{2n}O(C_aH_{2a}O)_wR^1$; n=2 to 4; a=2–4; w=1 to 30; $R^1$ is hydrogen, or a hydrocarbon radical between 1 and 4 carbon atoms; Q is $B(O)_jR^2 N(R^3)_2$ or $B(O)_jR^2N^+(R^3)_3$; B is a divalent bridging group of $C_1$ to $C_6$; $R^2$ is a divalent organic group containing 2 to 8 carbons, each optionally OH substituted; j is 0 or 1; $R^3$ is hydrogen, an amino alkyl of one to four carbons, an alkyl of 2 to 4 carbon atoms, an alkyl of 2 to 4 carbon atoms substituted with one or more hydroxy groups or a polyether of the general structure —$(C_aH_{2a}O)_bR^4$; each a is 2 to 4; each b is 2 to 30; the $R^4$ groups independently are hydrogen or a hydrocarbon group of 1 to 4 carbons; and P is Q or, provided f is not 0, methyl;

(b) a pesticide

16. An amino polyether siloxane of the following formula:

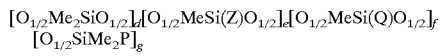

where d is 0 to 2; e is >0 and <4; f≧0 and <4; g is 2 if the siloxane is not cyclic or zero if the siloxane is cyclic; d+e+f+g≦6; $Z=C_nH_{2n}O(C_aH_{2a}O)_wR^1$; n=2 to 4; a=2–4; w=1 to 30; $R^1$ is hydrogen, or a hydrocarbon radical between 1 and 4 carbon atoms; $Q=B(O)_jR^2 N(R^3)_2$ or $B(O)_jR^2N^+(R^3)_3$; B is a divalent bridging group of $C_1$ to $C_6$; $R^2$ is a divalent organic group containing 2 to 8 carbons, each optionally OH substituted; j is 0 or 1; $R^3$ is hydrogen, an amino alkyl of one to four carbons, an alkyl of 2 to 4 carbon atoms an alkyl of 2 to 4 carbon atoms substituted with one or more hydroxy groups or a polyether of the general structure —$(C_aH_{2a}O)_bR^4$; each a is 2 to 4; each b is 2 to 30; the $R^4$ groups independently are hydrogen or a hydrocarbon group of 1 to 4 carbons.

17. A siloxane as in claim 16 wherein Q is $B(O)_jR^2N(R^3)_2$.

18. The composition of claim 2 wherein d is 0 to 2; e is >0 to 2; f is >0 to 2; a is from 2 to 3; B is divalent bridging group of $C_3$ to $C_4$; and $R^2$ is a divalent organic group containing 3 to 4 carbons.

19. The composition of claim 12 wherein d is 0 to 2; e is >0 to 2; f is >0 to 2; a is from 2 to 3; B is divalent bridging group of $C_3$ to $C_4$; and $R^2$ is a divalent organic group containing 3 to 4 carbons.

20. The process of claim 15 wherein d is 0 to 2; e is >0 to 2; f is >0 to 2; a is from 2 to 3; B is divalent bridging group of $C_3$ to $C_4$; and $R^2$ is a divalent organic group containing 3 to 4 carbons.

21. The amino polyether siloxane of claim 16 wherein d is 0 to 2; e is >0 to 2; a is from 2 to 3; B is divalent bridging group of $C_3$ to $C_4$; and $R^2$ is a divalent organic group containing 3 to 4 carbons.

22. The composition of claim 18 wherein n is 3; a is 2; w is 8; and $R^1$ is H.

23. The composition of claim 19 wherein n is 3; a is 2; w is 8; and $R^1$ is H.

24. The process of claim 20 wherein n is 3; a is 2; w is 8; and $R^1$ is H.

25. The amino polyether siloxane of claim 21 wherein n is 3; a is 2; w is 8; and $R^1$ is H.

26. The composition of claim 22 wherein $R^2$ is a hydroxy alkylene group; j is 1; and the $R^3$ groups are independently hydrogen, methyl, ethyl, hydroxyethyl or hydroxy propyl.

27. The composition of claim 23 wherein $R^2$ is a hydroxy alkylene group; j is 1; and the $R^3$ groups are independently hydrogen, methyl, ethyl, hydroxyethyl or hydroxy propyl.

28. The process of claim 24 wherein $R^2$ is a hydroxy alkylene group; j is 1; and the $R^3$ groups are independently hydrogen, methyl, ethyl, hydroxyethyl or hydroxy propyl.

29. The amino polyether siloxane of claim 25 wherein $R^2$ is a hydroxy alkylene group; j is 1; and the $R^3$ groups are independently hydrogen, methyl, ethyl, hydroxyethyl or hydroxy propyl.

30. The composition of claim 22 wherein $R^2$ is a hydroxy alkylene group; j is 1; and the $R^3$ groups are independently hydrogen, methyl, ethyl, hydroxyethyl or hydroxy propyl.

31. The composition of claim 23 wherein $R^2$ is a hydroxy alkylene group; j is 1; and the $R^3$ groups are independently hydrogen, methyl, ethyl, hydroxyethyl or hydroxy propyl.

32. The process of claim 24 wherein $R^2$ is a hydroxy alkylene group; j is 1; and the $R^3$ groups are independently hydrogen, methyl, ethyl, hydroxyethyl or hydroxy propyl.

33. The amino polyether siloxane of claim 25 wherein $R^2$ is a hydroxy alkylene group; j is 1; and the $R^3$ groups are independently hydrogen, methyl, ethyl, hydroxyethyl or hydroxy propyl.

* * * * *